US00PP36100P2

(12) United States Plant Patent
Lewers et al.

(10) Patent No.: US PP36,100 P2
(45) Date of Patent: Sep. 10, 2024

(54) STRAWBERRY PLANT NAMED 'USDA Lumina'

(50) Latin Name: ***Fragaria* x *ananassa* Duchesne ex Rozier**
Varietal Denomination: USDA Lumina

(71) Applicant: The United States of America, as represented by the Secretary of Agriculture, Washington, DC (US)

(72) Inventors: Kimberly S. Lewers, Columbia, MD (US); John Enns, Hyattsville, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 18/242,722

(22) Filed: Sep. 6, 2023

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
CPC ..... A01H 5/08; A01H 5/00; A01H 6/7409; A01H 6/74
See application file for complete search history.

(56) References Cited

U.S. PATENT DOCUMENTS

PP19,763 P2 * 2/2009 Ballington ..... A01H 6/7409 Plt./208

OTHER PUBLICATIONS

CPVO OCVV on p. 15, col. 5 at No. 40 retrieved on Feb. 6, 2024 at https://cpvo.europa.eu/sites/default/files/documents/TP/fruits/TP_022-2_Strawberry.pdf, 2009, pp. 1 and 15. (Year: 2009).*
International Code of Nomenclature for Cultivated Plants, ISHS Scripta Horticulturae No. 18, Ninth ed. 2016, 2 cover pages and p. 30. (Year: 2016).*

* cited by examiner

*Primary Examiner* — June Hwu
(74) *Attorney, Agent, or Firm* — John Fado; John Henri

(57) ABSTRACT

This invention relates to a new and distinct cultivar of strawberry plant named 'USDA Lumina'. The new early-season cultivar is primarily characterized by large, bright, glossy, sweet fruits resistant to anthracnose fruit rot.

3 Drawing Sheets

Latin name of the genus and species of the plant claimed: 'USDA LUMINA' is a new strawberry plant that is *Fragaria* x *ananassa* Duchesne ex Rozier.

Variety denomination: The new strawberry plant claimed is of the variety denominated 'USDA Lumina' *Fragaria* x *ananassa* Duchesne ex Rozier.

BACKGROUND OF THE NEW PLANT

The present invention relates to a new and distinct strawberry cultivar designated 'USDA Lumina'. This new strawberry cultivar was discovered in Beltsville, Maryland, in Spring 2019 and originated from a cross between the female parent B2475 (unpatented) and the male parent B2197 (unpatented). The original seedling of the new cultivar was asexually propagated in Beltsville since 2019 by rooting daughter plants from stolons of the mother plant. The present invention has been found to be stable and reproduce true to type through successive asexual propagations rooting daughter plants from stolons.

BRIEF SUMMARY OF THE INVENTION

The cultivar 'USDA Lumina' is an early-season strawberry cultivar resistant to anthracnose fruit rot. Fruit yields are higher than other early-season cultivars. It has sweet fruit which are very attractive, brightly colored, glossy, and with uniform symmetry.

DESCRIPTIONS OF THE PHOTOGRAPHS

The accompanying color photographs show typical specimens of the new cultivar at various stages of development as nearly true as it is possible to make color reproductions.

DESCRIPTION OF THE NEW CULTIVAR

Figure 1:
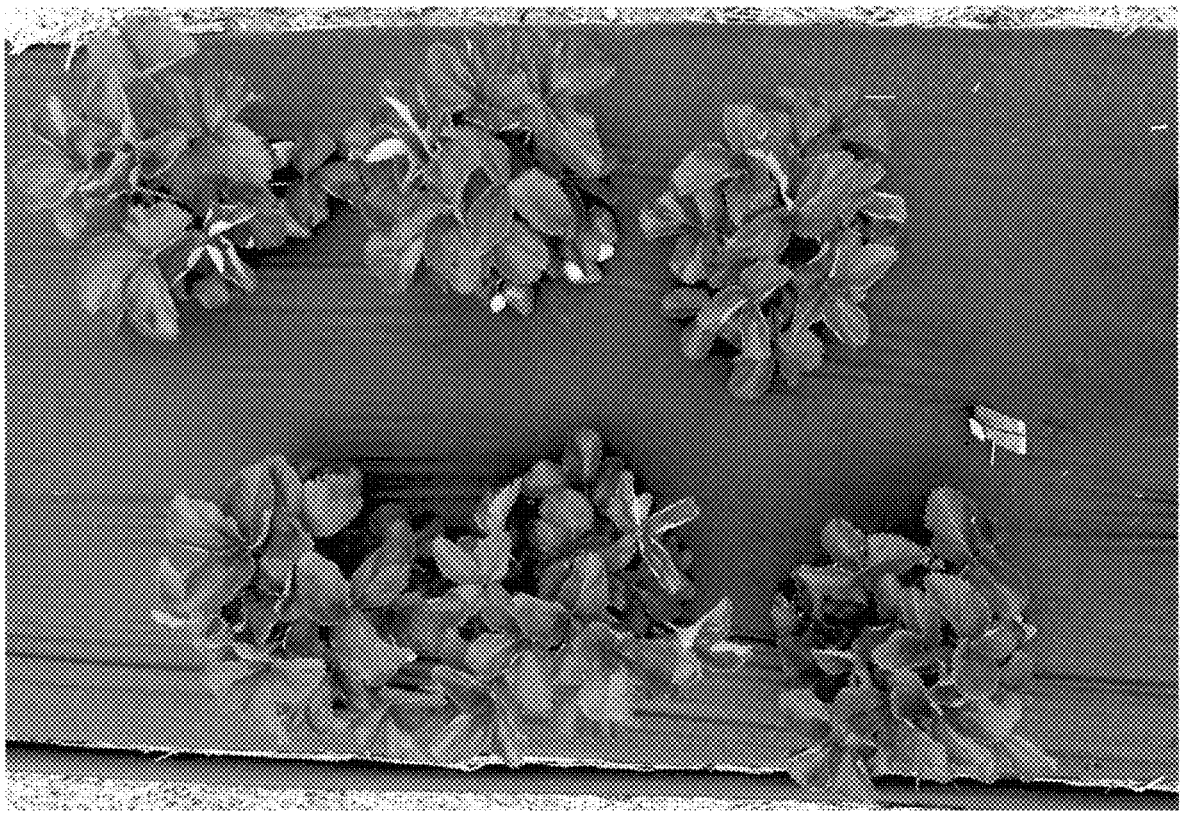
FIG. 1 shows a six-plant plot of 'USDA Lumina' during fruiting.
Figure 2:
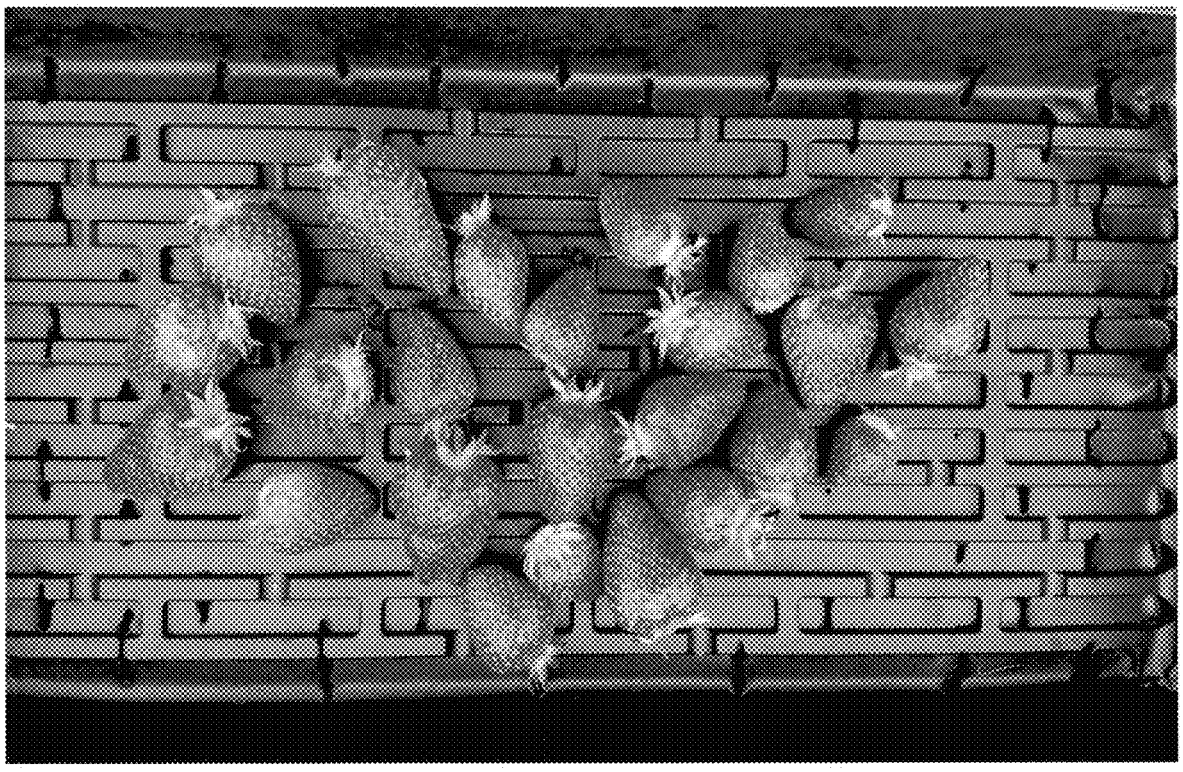
FIG. 2 shows the uniform shape and variation in size of 'USDA Lumina' fruit from a single harvest of a six-plant plot.
Figure 3:
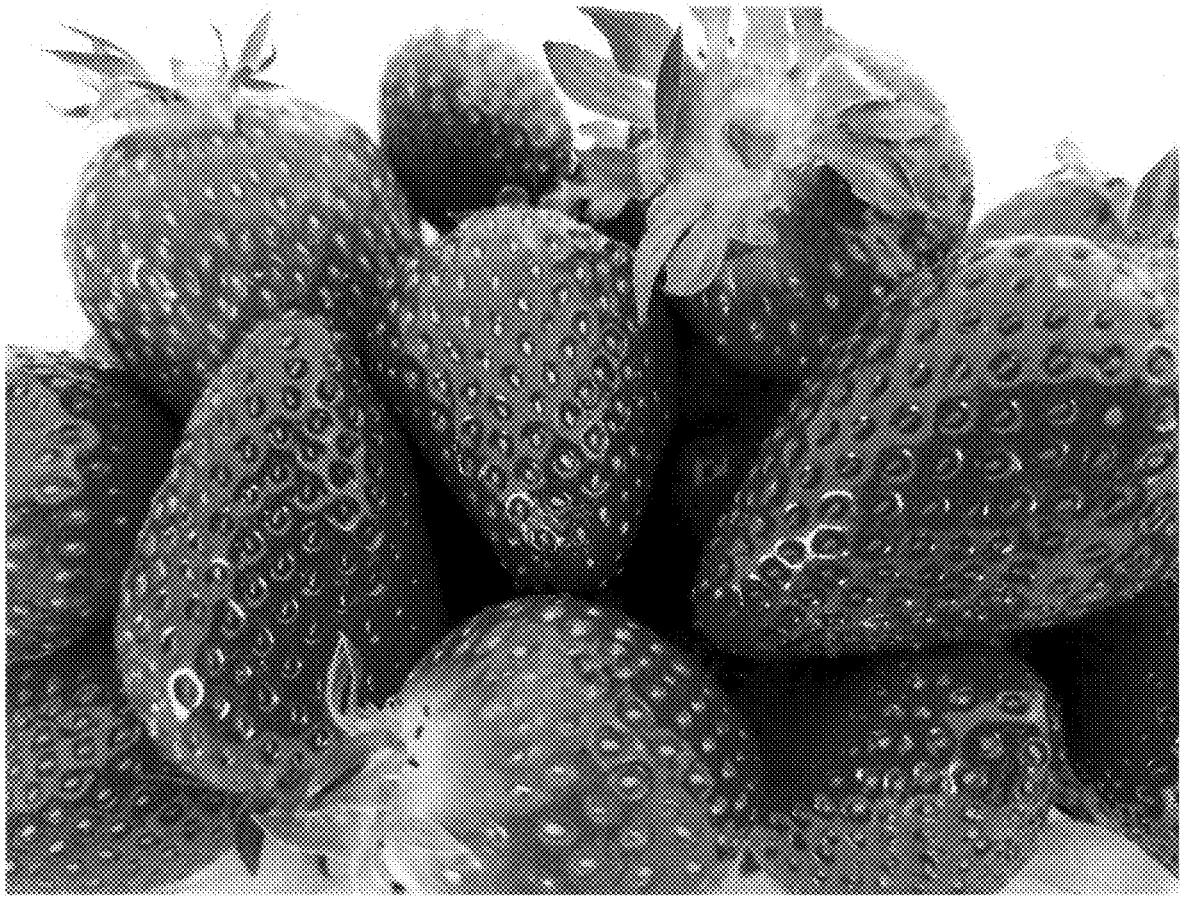
FIG. 3 shows the glossiness of 'USDA Lumina' fruit.

The following description of 'USDA Lumina' is based on observations taken from 2020 through 2023 growing seasons in in evaluations in Beltsville, Maryland, 2023 USDA Plant Hardiness Zone 7b. This description is in accordance with UPOV terminology. Color designations, color descriptions, and other phenotypical descriptions may deviate from the stated values and descriptions, depending on variation in environmental, seasonal, climatic, and cultural conditions. 'USDA Lumina' has not been observed under all possible environmental conditions. The botanical description of 'USDA Lumina' was taken from plants nine months after establishment in the field. Color terminology follows The Royal Horticultural Society Colour Chart, London (R.H.S.86).

DETAILED BOTANICAL DESCRIPTION

Table 1 shows selected characteristics of the new cultivar compared with plant characteristics of 'Earliglow' (unpatented) and 'Galletta' (U.S. Plant Pat. No. 19,763). Characteristics include fruit diameter and length, and the length/width ratio, average fruit weight, sweetness (Brix), acidity (pH and TA), and yield (weight and berry number).

TABLE 1

| Characteristic | 'USDA Lumina' | 'Earliglow' | 'Galletta' |
|---|---|---|---|
| Diameter fruit (cm) | 5.0 | 3.8 | 4.8 |
| Length fruit (cm) | 3.9 | 3.6 | 3.6 |
| Ratio fruit length/width | 1.3 | 1.1 | 1.3 |
| Weight fruit (g) | 14.1 | 6.9 | 17.1 |
| Brix (percent soluble solids) | 9.13 | 10.87 | 8.07 |
| pH | 3.73 | 3.67 | 3.58 |
| Titratable acidity (TA) | 0.92 | 1.01 | 0.89 |
| Yield (kg/plant) | 1.00 | 0.55 | 0.86 |
| Yield (non-decayed berries/plant) | 53.9 | 73.7 | 43.6 |

Table 2 shows plant characteristics of the new cultivar compared with plant characteristics of 'Earliglow' and 'Galletta'. Plant characteristics include plant height, diameter, number of crowns per plant, habit, density of individual plants and vigor.

TABLE 2

| Characteristic | 'USDA Lumina' | 'Earliglow' | 'Galletta' |
|---|---|---|---|
| Plant height (cm) | 23.5 | 20.8 | 18.5 |
| Plant diameter (cm) | 46.2 | 45.5 | 37.7 |
| Number of crowns plant | 5.3 | 4.2 | 2.5 |
| Habit | Upright open globose | Upright open globose | Upright open globose |
| Density of individual plant | Medium to dense | Medium | Not dense |
| Vigor | Medium to strong | Medium to strong | Medium |

Table 3 shows leaf characteristics of the new cultivar compared with leaf characteristics of 'Earliglow' and 'Galletta'. Leaf characteristics include leaf type, leaf shape, leaf length, leaf width, terminal leaflet length, terminal leaflet width, terminal leaflet length to width ratio, leaf margins, shape of teeth, leaf serrations per leaflet, upper and lower leaf surface color, number of leaflets, terminal leaflet apex shape, terminal leaflet base shape, glossiness upper side leaf surface, texture upper side leaf surface, texture underside leaf surface, and leaf arrangement.

TABLE 3

| Characteristic | 'USDA Lumina' | 'Earliglow' | 'Galletta' |
|---|---|---|---|
| Leaf type | Semi-evergreen | Semi-evergreen | Semi-evergreen |
| Leaf shape | Trifoliolate with ovate leaflets touching to overlapping | Trifoliolate with ovate leaflets touching to overlapping | Trifoliolate with ovate leaflets touching to overlapping |
| Leaf length (cm) | 12.8 | 15.0 | 12.9 |
| Leaf width (cm) | 16.0 | 17.3 | 15.9 |

TABLE 3-continued

| Characteristic | 'USDA Lumina' | 'Earliglow' | 'Galletta' |
|---|---|---|---|
| Terminal leaflet length (cm) | 8.7 | 8.8 | 8.3 |
| Terminal leaflet width (cm) | 6.9 | 7.8 | 7.1 |
| Terminal leaflet length width ratio | 1.3 | 1.1 | 1.2 |
| Leaf margins | Serrate | Serrate | Serrate |
| Shape of teeth | Apiculate | Apiculate | Apiculate |
| Leaf serrations per leaflet | 27.7 | 26.8 | 26.3 |
| Color mature leaves upper surface | Yellow-Green Group 146A | Green Group 137A | Green Group 137A |
| Color mature leaves lower surface | Yellow-Green Group 147B | Green Group 137C | Green Group 137C |
| Number of leaflets | 3 | 3 | 3 |
| Terminal leaflet apex shape | Obtuse | Obtuse | Obtuse |
| Terminal leaflet base shape | Acute cuneate | Acute cuneate | Acute cuneate |
| Glossiness upper side leaf surface | Semi-gloss | Semi-gloss | Semi-gloss |
| Texture upper side leaf surface | Very slightly rugose | Very slightly rugose | Very slightly rugose |
| Texture underside leaf surface | Very slightly reticulate | Very slightly reticulate | Very slightly reticulate |
| Leaf arrangement | Individual trifoliate leaves attached to compressed stem (crown) at ground level | Individual trifoliate leaves attached to compressed stem (crown) at ground level | Individual trifoliate leaves attached to compressed stem (crown) at ground level |

Table 4 shows information about the petiole, the petiolule, the bract and the stipule of the new cultivar compared to 'Farliglow' and 'Galletta'. This includes petiole length, petiole diameter, petiole pubescence, petiole color, petiolule color, petiolule length, petiole hair attitude, bract frequency and color, texture petiole, and stipule length, width and color.

TABLE 4

| Characteristic | 'USDA Lumina' | 'Earliglow' | 'Galletta' |
|---|---|---|---|
| Leaf petiole length (cm) | 15.0 | 16.9 | 12.6 |
| Petiole diameter (cm) | 0.36 | 0.32 | 0.41 |
| Petiole texture | Smooth | Smooth | Smooth |
| Petiole pubescence | Sparse | Very sparse | Moderately dense |
| Petiole hair attitude | Upwards to outwards | Outwards | Outwards |
| Petiole color | Yellow Green Group 144A | Yellow Green Group 144B | Yellow Green Group 144B |
| Petiolule color | Yellow Green Group 144A | Yellow Green Group 144B | Yellow Green Group 144B |
| Petiolule length (cm) | 0.84 | 0.52 | 0.58 |
| Bract frequency | 1 to 2 per florescence, generally unifoliate | 1 to 2 per florescence, generally unifoliate | 1 to 2 per florescence, generally unifoliate |
| Bract color | Yellow Green Group 144A | Yellow Green Group 144B | Yellow Green Group 144B |

TABLE 4-continued

| Characteristic | 'USDA Lumina' | 'Earliglow' | 'Galletta' |
|---|---|---|---|
| Stipule length (cm) | 3.6 | 3.1 | 2.8 |
| Stipule width (cm) | 0.59 | 0.49 | 0.70 |
| Stipule color | Yellow Green Group 144A, Grayish Red Group 182B | Yellow Green Group 144B, Grayish Red Group 182B | Yellow Green Group 144B, Grayish Red Group 182B |

Table 5 shows stolon characteristics of the new cultivar compared to 'Farliglow' and 'Galletta'. These characteristics include the number of stolons, the anthocyanin coloration of the stolons, the thickness of the stolons, and the pubescence of the stolons.

TABLE 5

| Characteristic | 'USDA Lumina' | 'Earliglow' | 'Galletta' |
|---|---|---|---|
| Stolon production per plant | 9.3 | 2.3 | 7.7 |
| Stolon color | Yellow Green Group 144A, Grayish Red Group 182B | Yellow Green Group 144B, Grayish Red Group 182B | Yellow Green Group 144B, Grayish Red Group 182B |
| Stolon anthocyanin | Medium | Strong | Medium |
| Stolon thickness (cm) | 0.27 | 0.28 | 0.26 |
| Stolon pubescence | Medium | Medium | Medium |

Table 6 shows inflorescence characteristics of the new cultivar compared to 'Earliglow' and 'Galletta'. These characteristics include inflorescence position relative to foliage, flower type, flower size, petal shape, relative petal spacing, petal apex shape, petal margin, petal base shape, petal length, petal width, petal length/width ratio, number of petals, petal color, Stigma color, style color, anther color, filament color, and flower truss type.

TABLE 6

| Characteristic | 'USDA Lumina' | 'Earliglow' | 'Galletta' |
|---|---|---|---|
| Inflorescence position | Slightly below to level | Level to slightly above | Slightly below to level |
| Flower type | Complete simple | Complete simple | Complete simple |
| Flower diameter (cm) | 3.1 | 2.3 | 1.9 |
| Petal shape | Circular to obovate | Circular to obovate | Circular to obovate |
| Petal spacing | Overlapping | Separate to overlapping | Overlapping |
| Petal apex shape | Circular | Circular | Circular |
| Petal margin | Entire | Entire | Entire |
| Petal base shape | Obovate | Obovate | Obovate |
| Petal length (cm) | 1.16 | 0.91 | 0.82 |
| Petal width (cm) | 1.14 | 0.74 | 0.93 |
| Petal length/width ratio | 1.02 | 1.25 | 0.88 |
| Petal count | 5.0 | 5.0 | 5.2 |
| Petal color | White Group 155D | White Group 155D | White Group 155D |

TABLE 6-continued

| Characteristic | 'USDA Lumina' | 'Earliglow' | 'Galletta' |
|---|---|---|---|
| Stigma color | Yellow-Orange Group 20C | Yellow-Green Group 150C | Yellow-Orange Group 18B |
| Style color | Yellow-Green Group 150B | Yellow-Green Group 154B | Yellow-Green Group 151D |
| Anther color | Yellow-Orange Group 20A | Yellow-Orange Group 21A | Yellow-Orange Group 21B |
| Filament color | Yellow-Green Group 150C | Yellow-Green Group 154C | Yellow-Green Group 154D |
| Anther count | 23.6 | 22.3 | 24.6 |
| Blooming habit | Cyme | Cyme | Cyme |

Table 7 shows fruit characteristics of the new cultivar compared to 'Earliglow' and 'Galletta'. These characteristics include number of berries per truss, fruiting truss attitude, fruit length, fruit diameter, fruit length/width ratio, fruit weight, relative fruit size, predominant fruit shape, difference in shape between primary and secondary fruit, band without achenes, evenness of fruit surface, top color, non-blush side color, blush side color, internal color, achene color, achene count per fruit, insertion of calyx, pose of calyx segments, size of calyx in relation to fruit, ease of calyx removal, firmness of flesh, evenness of flesh color, distribution of flesh color, sweetness, acidity, Brix, pH, titratable acidity, texture when tasted, time of flowering, harvest maturity (50% of plants with ripe fruit), type of bearing, and yield.

TABLE 7

| Characteristic | 'USDA Lumina' | 'Earliglow' | 'Galletta' |
|---|---|---|---|
| Number of berries per fruiting truss | 5.0 | 7.7 | 5.7 |
| Fruiting truss attitude | Prostrate | Prostrate | Prostrate |
| Diameter fruit (cm) | 5.0 | 3.8 | 4.8 |
| Length fruit (cm) | 3.9 | 3.6 | 3.6 |
| Ratio fruit length/width | 1.3 | 1.1 | 1.3 |
| Weight fruit (g) | 14.1 | 6.9 | 17.1 |
| Relative fruit size | Medium to Large | Small | Medium to Large |
| Predominant fruit shape | Ovate to conic | Conic with neck | Ovate to conic |
| Difference in shape between primary and secondary fruits | None, uniform | None, uniform | Moderate, primaries have some ridging |
| Band without achenes | Slight | Moderate | None to slight |
| Evenness of fruit surface | Even to slightly uneven | Slightly uneven | Even to slightly uneven |
| Color of top of fruit | Red Group 44A | Red Group 46B | Red Group 45A |
| Blush side color | Red Group 45A | Red Group 46A | Red Group 46A |
| Non-blush side color | Red Group 44B | Red Group 44A | Red Group 45A |
| Internal flesh color | Orange-White Group 159D, Red Group 44A, Red Group 44C | White Group 155D, Red Group 44A | Orange-White Group 159D, Red Group 44A, Red Group 44C |
| Achene position | At surface | At surface | At surface to slightly raised |
| Achene color | Red Group 45A, Yellow | Red Group 46B, Yellow-Green | Yellow-Green Group 153B, |

TABLE 7-continued

| Characteristic | 'USDA Lumina' | 'Earliglow' | 'Galletta' |
|---|---|---|---|
| | Group 153A, Yellow-Green Group 152C | Group 152C, Greyed-Orange Group 166A | Greyed-Orange Group 166B |
| Achene count | 305 | 252 | 304 |
| Insertion of calyx | At surface to slightly necked | Necked | At surface to necked |
| Pose of calyx segments | Reflexed | Reflexed | Reflexed |
| Size of calyx in relation to fruit | Smaller to slightly larger | Same to slightly larger | Same to slightly larger |
| Ease of calyx removal | Difficult | Difficult | Difficult |
| Firmness of flesh | Medium to firm | Medium | Medium to firm |
| Evenness of flesh color | Uneven | Uneven | Uneven |
| Distribution of flesh color | Red Group 44C core, Orange-White Group 159D halo, area near calyx, and radiant lines, through Red Group 44A outer ring | Red Group 44A core, then White Group 155D halo and radiant lines, through Red Group 44A outer ring | Red Group 44C core, Orange-White Group 159D area near calyx and radiant lines through Red Group 44A outer ring |
| Sweetness | Sweet | Very sweet | Mild |
| Acidity | Mild | Medium | Tart |
| Brix (percent soluble solids) | 9.13 | 10.87 | 8.07 |
| pH | 3.73 | 3.67 | 3.58 |
| Titratable acidity (TA) | 0.92 | 1.01 | 0.89 |
| Texture when tasted | Smooth to Creamy | Fine, somewhat smooth | Fine, somewhat smooth, slightly gummy |
| Time of flowering | April to May | April to May | April to May |
| Harvest maturity (50% of plant with ripe fruit) | Mid to late May | Mid to late May | Mid to late May |
| Type of bearing | Short Day/ June Bearing | Short Day/ June Bearing | Short Day/ June Bearing |

TABLE 7-continued

| Characteristic | 'USDA Lumina' | 'Earliglow' | 'Galletta' |
|---|---|---|---|
| Yield (non-decayed berries/ plant) | 53.9 | 73.7 | 43.6 |
| Yield (kg/plant) | 1.00 | 0.55 | 0.86 |

Table 8 shows the fruit quality of the new cultivar compared to 'Earliglow' and 'Galletta' after one week and two weeks in refrigerated storage. The postharvest fruit quality characteristics include the percentage of stored fruits that are marketable, degraded, or rotted after one week and two weeks in refrigerated storage.

TABLE 8

| | Percentage marketable | | Percentage degraded | |
|---|---|---|---|---|
| Cultivar | Week 1 | Week 2 | Week 1 | Week 2 |
| 'USDA Lumina' | 91 bcd | 53 bc | 45 bcd | 94 bcd |
| 'Earliglow' | 98 a | 51 bc | 46 bcd | 97 abc |
| 'Galletta' | 95 ab | 42 cde | 28 d | 98 a |

| | Percentage rotted | |
|---|---|---|
| Cultivar | Week 1 | Week 2 |
| 'USDA Lumina' | 2 cde | 20 abc |
| 'Earliglow' | 1 e | 2 ef |
| 'Galletta' | 1 e | 1 f |

COMPARISON WITH PARENTAL GENOTYPES

When 'USDA Lumina' is compared to female parent, B2475 (unpatented), the fruits have better symmetry and are less susceptible to Botrytis fruit rot. When 'USDA Lumina' is compared to male parent, B2197 (unpatented), the fruits a more desirable, less mealy texture and are less susceptible to *Botrytis* fruit rot.

We claim:

1. A new and distinct cultivar of strawberry plant named 'USDA Lumina', substantially as described and illustrated herein.

* * * * *